(12) United States Patent
Charles et al.

(10) Patent No.: US 12,070,280 B2
(45) Date of Patent: Aug. 27, 2024

(54) VOICE-CONTROLLED SURGICAL SYSTEM (71) Applicant: Alcon Inc., Fribourg (CH)

(72) Inventors: Steven T. Charles, Memphis, TN (US); Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 94 days.

(21) Appl. No.: 17/649,591

(22) Filed: Feb. 1, 2022

(65) Prior Publication Data

US 2022/0249178 A1 Aug. 11, 2022

Related U.S. Application Data

(60) Provisional application No. 63/146,126, filed on Feb. 5, 2021.

(51) Int. Cl.
*A61B 90/00* (2016.01)
*A61B 34/00* (2016.01)
*A61B 17/00* (2006.01)

(52) U.S. Cl.
CPC ............ *A61B 34/25* (2016.02); *A61B 90/361* (2016.02); *A61B 2017/00203* (2013.01)

(58) Field of Classification Search
CPC .............................. A61B 34/25; A61B 90/361
(Continued)

(56) References Cited

U.S. PATENT DOCUMENTS 4,989,253 A    1/1991 Liang et al.
6,496,099 B2 * 12/2002 Wang ..................... G16H 40/40
                                                                        606/1
(Continued)

FOREIGN PATENT DOCUMENTS

WO    2014185954 A1    11/2014
WO    2018000449 A1    1/2018

OTHER PUBLICATIONS

TI Designs: TIDEP-0088—Audio Pre-Processing System Reference Design for Voice-Based Applications Using the 66AK2Gx SoC; Accessed at https://www.ti.com/lit/ug/tiducr7a/tiducr7a.pdf?ts=1654867926058&ref_url=https%253A%252F%252Fwww.ti.com%252Ftool%252FTIDEP-0088; Accessed on Jun. 10, 2022, Article dated May 2017; Revised Jun. 2018 (24 pages).

*Primary Examiner* — Nadia A Mahmood (57) ABSTRACT

Certain aspects of the present disclosure provide a voice-controlled system for controlling devices and systems in a surgical setting. The voice-controlled system includes at least one microphone and at least one loudspeaker distributed within the surgical setting to receive and audibly respond to voice commands from operating staff. In certain aspects, the at least one microphone and at least one loudspeaker include a phased microphone array and a phased loudspeaker array that are coordinated and synchronized to perform active noise reduction, echo cancellation, and directional determination of sound sources. The voice-controlled system performs tasks, such as activation of surgical devices, based on verbal interactions with the operating staff through the at least one microphone and at least one loudspeaker. In certain aspects, the voice-controlled system is configured to recognize, decipher, and prioritize natural language commands from different operating staff, and further provides pre-programming of device settings and operating staff pre-sets.

16 Claims, 3 Drawing Sheets

(58) Field of Classification Search
USPC .......................................................... 606/1
See application file for complete search history.

(56) References Cited

U.S. PATENT DOCUMENTS

| | | |
|---|---|---|
| 6,591,239 B1 | 7/2003 | Mccall et al. |
| 7,286,992 B2 | 10/2007 | Sander et al. |
| 7,383,181 B2 | 6/2008 | Huang et al. |
| 7,400,752 B2 | 7/2008 | Zacharias |
| 7,657,433 B1 | 2/2010 | Chang |
| 7,716,057 B2 | 5/2010 | Horvitz |
| 7,853,453 B2 | 12/2010 | Potter |
| 8,660,847 B2 | 2/2014 | Soemo et al. |
| 8,755,531 B2 | 6/2014 | Bergere |
| 9,031,268 B2 | 5/2015 | Fejzo et al. |
| 9,031,847 B2 | 5/2015 | Sarin et al. |
| 9,548,048 B1 | 1/2017 | Solh et al. |
| 9,681,982 B2 | 6/2017 | Yacono |
| 9,844,321 B1 | 12/2017 | Ekvall |
| 9,966,059 B1 | 5/2018 | Ayrapetian et al. |
| 9,986,412 B2 | 5/2018 | Keränen et al. |
| 10,032,451 B1 | 7/2018 | Mamkina et al. |
| 10,032,463 B1 | 7/2018 | Rastrow et al. |
| 10,192,550 B2 | 1/2019 | Froelich |
| 10,304,444 B2 | 5/2019 | Mathias et al. |
| 10,305,766 B1 | 5/2019 | Zhang et al. |
| 10,373,612 B2 | 8/2019 | Parthasarathi et al. |
| 10,388,274 B1 | 8/2019 | Hoffmeister |
| 10,438,576 B2 | 10/2019 | Todd et al. |
| 10,490,183 B2 | 11/2019 | Singh et al. |
| 10,490,195 B1 | 11/2019 | Krishnamoorthy et al. |
| 10,515,625 B1 | 12/2019 | Metallinou et al. |
| 10,522,134 B1 | 12/2019 | Matsoukas et al. |
| 10,918,450 B2 | 2/2021 | Martin |
| 11,147,636 B2 | 10/2021 | Hallen |
| 2002/0166557 A1 | 11/2002 | Cooper |
| 2009/0175464 A1 | 7/2009 | Somen et al. |
| 2009/0248041 A1 | 10/2009 | Williams et al. |
| 2010/0100080 A1 | 4/2010 | Huculak et al. |
| 2016/0125882 A1 | 5/2016 | Contolini et al. |
| 2017/0212723 A1 | 7/2017 | Atarot et al. |
| 2018/0168755 A1 | 6/2018 | Cagle et al. |
| 2019/0290121 A1 | 9/2019 | Fava |
| 2020/0152190 A1 | 5/2020 | Itkowitz et al. |
| 2021/0186624 A1 | 6/2021 | Charles |

* cited by examiner

VOICE-CONTROLLED SURGICAL SYSTEM

PRIORITY CLAIM

This application claims the benefit of priority of U.S. Provisional Patent Application Ser. No. 63/146,126 titled "VOICE-CONTROLLED SURGICAL SYSTEM," filed on Feb. 5, 2021, whose inventors are Steven T. Charles and Paul R. Hallen, which is hereby incorporated by reference in its entirety as though fully and completely set forth herein.

FIELD

The present disclosure generally relates to surgical devices and systems, and more specifically, to voice-activated control systems for surgical devices and systems.

BACKGROUND

Many surgical procedures, including ophthalmic procedures such as refractive cataract surgery and vitreoretinal surgery, are extremely challenging and require more than one operating staff member to adjust various apparatuses in the operating room, such as the lighting, operating table, microscope, viewing devices, and surgical tools and/or consoles. The presence of multiple operating staff enables a surgeon to continue his or her work without the need to stop and change the settings of a desired apparatus. However, simultaneous and seamless operation of separate devices or systems by multiple operating staff is a major challenge during surgical procedures, and in particular, ophthalmic procedures. Furthermore, extra personnel add cost to the procedure and additional burden on resources within the operating room, such as floor space, while also increasing the risk of contamination therein.

Recently, voice-activated applications have been utilized to mitigate some of the challenges of complex surgical procedures, thereby enabling voice-control of surgical devices without the need for physical interaction by operating staff and reducing the amount of personnel required for surgical procedures. Yet, current voice-controlled surgical devices and systems have several limitations, such as the inability to recognize, discern, and prioritize between personnel providing voice commands to control the devices. Additionally, in certain examples, the number and spatial arrangement of microphones within a high-noise operating room is suboptimal, leading to undetected or misinterpreted voice commands from operating staff due to issues with background noise and sound clarity. Still further, in certain examples, operating staff must learn predetermined command input syntax to effectively execute desired device functions, rather than using conversational or natural language commands.

Accordingly, there is a need in the art for improved voice-controlled surgical systems.

SUMMARY

The present disclosure relates to surgical devices and systems, and more particularly, to voice-activated control systems for surgical devices and systems.

According to certain embodiments, a surgical command system is provided. The surgical command system includes a processor, one or more microphones configured to convert sound waves within a surgical operating environment to one or more audio input signals relayed to the processor, one or more loudspeakers configured to generate sound waves within the surgical operating environment based on one or more audio output signals received directly or indirectly from the processor, and a memory comprising executable instructions in data communication with the processor. The processor is configured to execute the instructions to cause the surgical command system to directly or indirectly receive the one or more audio input signals from the one or more microphones, identify one or more speech commands in the one or more audio input signals, map at least one of the one or more speech commands to a user in the surgical operating environment, and identify one or more actions associated with the at least one of the one or more speech commands. The processor is further configured to indicate the one or more actions to a surgical device to cause the surgical device to perform the one of more actions, cause the one or more audio output signals to be produced based on the one or more actions, and cause the one or more loudspeakers to generate outgoing speech responses based on the one or more audio output signals.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the Figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Embodiments of the present disclosure generally relate to a voice-controlled system for controlling devices and systems in a surgical setting, such as an ophthalmic surgical setting. In certain aspects, the voice-controlled system includes one or more phased microphone arrays (a phased microphone array refers to a plurality of microphones arranged in a phased array) and one or more phased loudspeaker arrays (a phased loudspeaker array refers to a plurality of loudspeakers arranged in a phased array). In certain aspects, the one or more phased microphone arrays are distributed throughout the surgical setting to identify and receive voice commands from operating staff. Further, one or more phased loudspeaker arrays may be distributed throughout the surgical setting to output audio responses and other audible signals to the operating staff. In certain aspects, the one or more phased microphone arrays are coordinated and synchronized to perform active noise reduction, echo cancellation, and directional determination of sound sources. In certain aspects, the voice-controlled system performs tasks, such as activation of surgical devices, primarily based on conversational or natural language interactions with the operating staff through the one or more phased microphone and loudspeaker arrays. In certain aspects, the voice-controlled system is configured to decipher, learn, recognize, and prioritize verbal commands from different operating staff, and further provides pre-programming of device settings and operating staff pre-sets.

As used herein, the term "surgical setting" may refer to any environment where surgical procedures are performed. For example, the term "surgical setting" may refer to an operating room, with one or more surgeons and operating staff involved in the surgical setting.

As used herein, the term "surgical system" may refer to any surgical system, console, or device for performing a surgical procedure. For example, the term "surgical system" may refer to a surgical tool or system, such as a phacoemulsification console, a laser system, an imaging system, an intraocular lens (IOL) alignment system, a biometer, an optical coherence tomography (OCT) machine, or a vitrectomy console.

Although generally described with reference to an ophthalmic surgical setting, the devices and systems described herein may be implemented in other settings and contexts, such as other surgical settings, without departing from the scope of the present application.

As used herein, the term "about" may refer to a +/−10% variation from the nominal value. It is to be understood that such a variation can be included in any value provided herein.

Figure 1:
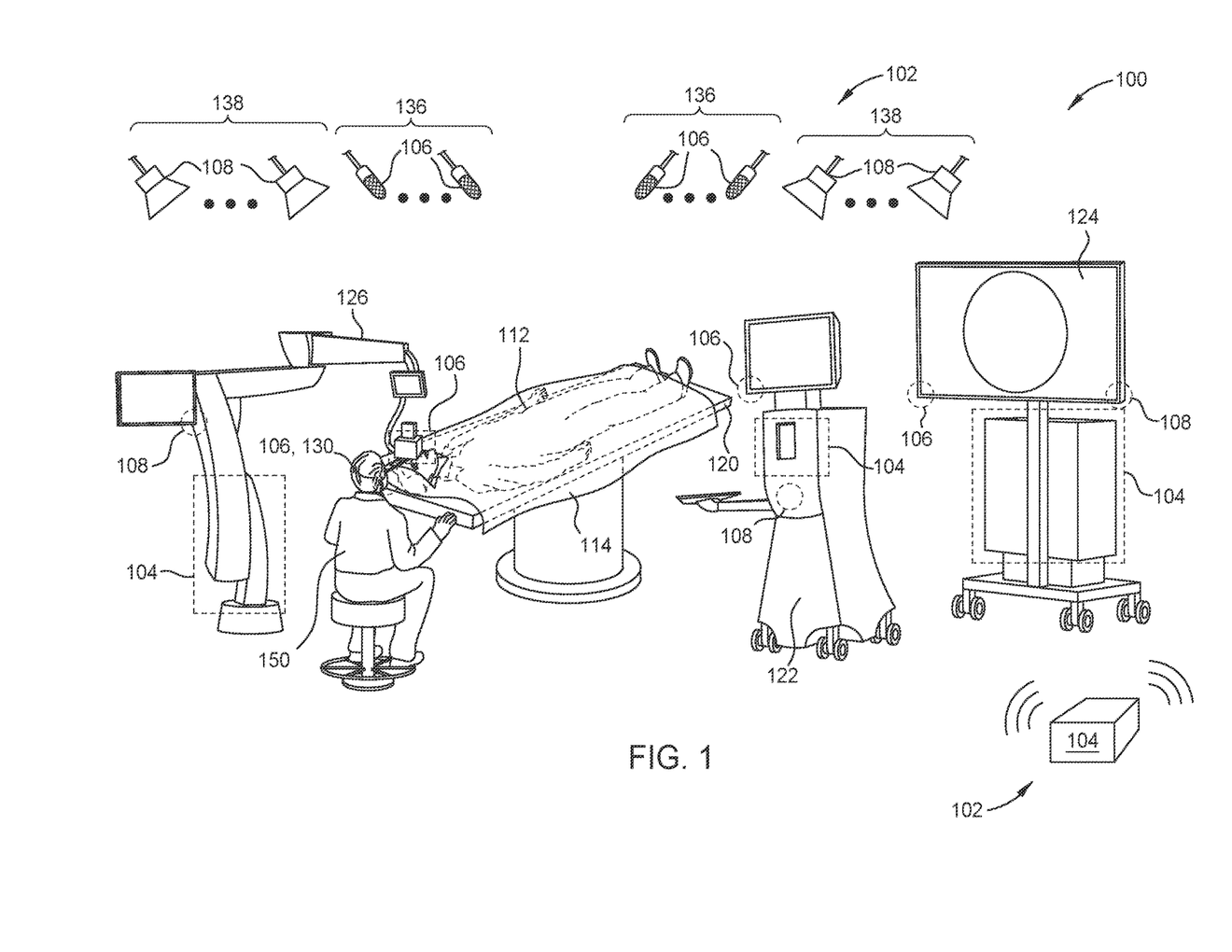
FIG. 1 illustrates a surgical setting with a voice-controlled surgical command system, in accordance with certain embodiments of the present disclosure.

FIG. 1 illustrates an example of a surgical setting 100 with a voice-controlled surgical command system 102, such as an ophthalmic surgical setting, in which a surgeon 150, one or more additional operating staff, and a patient 112 are present, according to certain embodiments of the present disclosure. Although one surgeon 150 is illustrated in FIG. 1, multiple surgeons and/or operating staff may use the surgical command system 102. For example, in certain embodiments, a surgical assistant and/or circulating nurse (i.e., circulator) may also be present within the surgical setting 100 and utilize the surgical command system 102.

As shown, the surgical command system 102 includes a surgical command controller 104 in direct or indirect communication with one or more surgical systems, consoles, and/or devices (e.g., integrated in an inter-networked surgical suite) within the surgical setting 100, such as an operating table 120, a surgical console 122, a heads-up display 124, and a microscope system 126. Examples of suitable surgical systems that may be included in the surgical suite include surgical consoles for performing vitreoretinal procedures, cataract surgeries, corneal transplants, glaucoma surgeries, LASIK (Laser Assisted In Situ Keratomileusis) surgeries, refractive lens exchanges, trabeculectomies, and refractive surgeries, among other consoles, imaging devices, laser devices, diagnostic devices, and accessories identifiable by those of ordinary skill.

In certain embodiments, the surgical command controller 104 is a stand-alone device or module (including a processor and a memory) that is in wireless or wired communication with one or more surgical systems physically positioned within the surgical setting 100. In certain other embodiments, however, the surgical command controller 104 includes one or more processors and/or memory integrated within one or more of the surgical systems physically positioned within the surgical setting 100. For example, the surgical command controller 104 may be integrated with the surgical console 122, heads-up display 124, and/or microscope 126, as illustrated by phantom elements 104 in FIG. 1. In certain aspects, the surgical command controller 104 refers to a set of software instructions that a processor associated with at least one of the surgical systems, physically positioned within the surgical setting 100, is configured to execute. In certain aspects, the operations of the surgical command controller 104 may be executed partly by the processor associated with the surgical command controller 104 and partly in a private or public cloud.

The surgical command system 102 further includes one or more pluralities of microphones 106 arranged in phased arrays 136 and one or more pluralities of loudspeakers 108 arranged in phased arrays 138. The microphones 106 and loudspeakers 108 are in wireless or wired communication with the surgical command controller 104, thus enabling the controller 104 to receive voice commands provided by the surgeon 150 and other operating staff, and further produce directional audible responses to the voice commands. In certain embodiments, the microphones 106 and/or loudspeakers 108 are distributed within the surgical setting 100 in close proximity to desired users (e.g., the surgeon 150, surgical assistant, and/or circulating nurse) from which the voice commands are to be received. In certain embodiments, however, the microphones 106 and/or loudspeakers 108 are widely dispersed within the surgical setting 100 to provide greater coverage of the surgical setting 100.

Similar to the surgical command controller 104, the microphones 106 and/or loudspeakers 108 may be stand-alone devices or may be physically integrated with one or more other surgical systems within the surgical setting 100. For example, the microphones 106 and/or loudspeakers 108 may be physically integrated into various components of the surgical console 122, heads-up display 124, and/or microscope 126, as illustrated by phantom elements 106 and 108 in FIG. 1. In certain embodiments, one or more phased microphone arrays 136 oriented toward (i.e., facing) one or more users within the surgical setting 100 for directional listening, thus enabling focusing of desired sounds (i.e., voice commands) and suppression of undesired sounds during capture and identification of voice commands in a noisy environment. For example, in certain embodiments, the microscope 126 may include at least one set of "forward-facing" microphones 106 for listening to the surgeon 150, and at least another set of "peripheral" microphones 106 oriented at 90° or 180° relative to the forward-facing microphones 106 for listening to an operating staff member (e.g., during a surgical procedure, the surgical assistant may be located at positions 90° or 180° from the surgeon 150 with respect to the microscope 126). In further embodiments, one or more sets of microphones 106 may be physically integrated into a surgical face mask 130, headset, cap, lavalier, visor, glasses, or other accessory worn by the surgeon 150 or other operating staff during a surgical procedure. In such embodiments, the microphones 106 may be disposable microphones, or hybrid reusable-and-disposable microphones configured to be utilized with replaceable single-use filters.

The microphones 106 and/or loudspeakers 108 include any suitable microphones and/or loudspeakers arranged in a phased array to perform beamforming (e.g., beamsteering) in order to facilitate directional listening, sound source localization and voice recognition, directional audio output (e.g., text-to-speech output), and audio signal quality enhancement. For example, the microphones 106 perform receive beamforming, or receive-side beamforming, while the loudspeakers 108 perform transmit beamforming, or transmit-side beamforming. In certain embodiments, the beamforming microphones 106 arranged in phased arrays 136 may enable the surgical command controller 104 to continuously detect a position of and localize a desired sound source (e.g., a user providing voice commands) among many sources, and further capture and amplify the sound waves emitted by the source while reducing or ignoring background noise, reverberation, and feedback to enhance signal-to-noise ratio and voice recognition accuracy. For example, during a typical ophthalmic surgical procedure, the surgeon 150 sits at either a side or top of the patient's head and near a microscope or other surgical device, while the surgical assistant is near the side of the patient's head and the circulating nurse moves around to several discrete locations within the surgical setting 100. In such an example, the microphones 106 may detect a given voice command as originating from one of the aforementioned positions, thereby enabling the surgical command system 102 to identify the source of the voice command as either being the surgeon 150, surgical assistant, or circulating nurse.

Furthermore, the loudspeakers 108, in synchronization with the microphones 106, enable the surgical command controller 104 to produce directional audible responses, outputs, signals, and alerts to desired users within the surgical setting 100. For example, upon detection of a voice command and a position of either the surgeon 150, surgical assistant, or circulating nurse generating the voice command, the surgical command controller 104 may send a directional text-to-speech-type response targeted toward the aforementioned users as appropriate, which, in certain embodiments, may be preceded by a user's name or other identifier. The directional response is output from the loudspeakers 108 and, in some examples, is directed via beamforming towards the user who issued the voice command, thereby increasing the likelihood that the commanding user is able hear the response more clearly, e.g., in comparison to other persons in the room. A directional response may also be advantageous because it may seem, to the commanding user, as if the response originated from the system or device the commanding user was addressing. The directionality of the responses and other outputs thus facilitates improved hearing thereof by operating staff within the surgical setting 100, and is also less likely to elicit a response from or worry the patient 112.

In order to further enhance the quality of audio received by the microphones 106, the microphones 106, loudspeakers 108, and surgical command controller 104 are synchronized to perform active noise reduction ("ANR") to eliminate or reduce continuous background noise such as noises produced by heating, ventilation, and cooling (HVAC) systems and surgical system and/or computer cooling fans. Additionally, the microphones 106, loudspeakers 108, and surgical command controller 104 are configured to synchronously perform acoustic echo suppression or echo cancellation to more cleanly capture voice commands provided by the surgeon 150 and/or operating staff. In certain embodiments, the microphones 106 within the surgical setting 100 are tuned for high and/or low frequency sounds, and may be each utilized independently or in combination with other microphones 106. Similarly, the loudspeakers 108 within the surgical setting 100 may each be utilized independently or in combination with other loudspeakers 108.

In certain embodiments, the microphones 106 and/or loudspeakers 108 distributed within the surgical setting 100 may be utilized by the surgeon 150 and/or other operating staff to listen to music and place or receive phone calls. In such embodiments, the microphones 106 and/or loudspeakers 108 may connect to a user's (e.g., the surgeon's) own mobile device via Bluetooth connection. When a phone call is placed or received by a user, the surgical command system 102 may give priority to the phone call and automatically mute music playing through the loudspeakers 108.

In further embodiments, the surgical command system 102 includes one or more microphones 106 and/or loudspeakers 108 directed toward and arranged in the vicinity of the patient 112, who is depicted as lying on the operating table 120 in FIG. 1. For example, one or more microphones 106 and/or loudspeakers 108 (individual devices or arranged in phased arrays) may be disposed on or integrated with the operating table 120, a patient headrest, and/or under a drape 114 that covers the patient 112 during a surgical procedure. The microphones 106 and/or loudspeakers 108 may provide a communication channel between the patient 112 and an operating staff member inside or outside the surgical setting 100, such as the surgeon 150, surgical assistant, and/or circulating nurse, for improving intelligibility during communication therebetween as well as addressing hearing loss or removed patient hearing aids. For example, the microphones 106 and/or loudspeakers 108 may enable the surgeon 150 to more clearly speak to the patient 112 in order to provide the patient 112 with instructions and information, or calm the patient 112 during the surgical procedure. In certain embodiments, the loudspeakers 108 may be utilized to provide soothing music to the patient 112, which further reduces the chance of the patient 112 listening to conversations between operating staff members. In such embodiments, patient music may be provided on separate channel from music provided to the surgeon 150 and/or other operating staff, thus enabling the patient's music to continue while a phone call is placed or received through the other microphones 106 and/or loudspeakers 108 within the surgical setting 100.

Note that, although the microphones 106 and loudspeakers 108 are generally described above as being arranged in beamforming phased arrays, individual directional microphones 106 and loudspeakers 108 positioned near the surgeon 150, surgical assistant, circulating nurse, and/or patient 112 (e.g., under the drape 114) are also within the scope of the disclosure.

As discussed in greater detail below with reference to FIG. 2 and FIG. 3, the surgical command system 102 interfaces (e.g., wirelessly or wired) with the one or more devices and/or systems (e.g., surgical console 122, heads-up display 124, and microscope 126) within the surgical setting 100 to take one or more actions for operating the devices and/or systems. The actions are based on voice commands provided by the surgeon 150 or other operating staff within the surgical setting 100 that are received by the one or more phased microphone arrays 136 distributed therein. In certain embodiments, the surgical command system 102 can control (e.g., activate, deactivate, change operational parameters, etc.) the various devices and/or systems within the surgical setting 100, adjust device settings, navigate a display dashboard (Graphical User Interface (GUI)/Human Machine Interface (HMI)), control diagnostic devices, and provide alerts and/or recommendations to the surgeon 150 and other operating staff via the phased array of loudspeakers 108. With speech interaction, the surgical command system 102 enables essentially "hands-free" surgical system control, thus improving surgical procedure efficiency by reducing the amount of movement and/or "hands-on" device operation required of the surgeon 150 and other operating staff, who may have their hands already occupied with other tasks.

Figure 2:
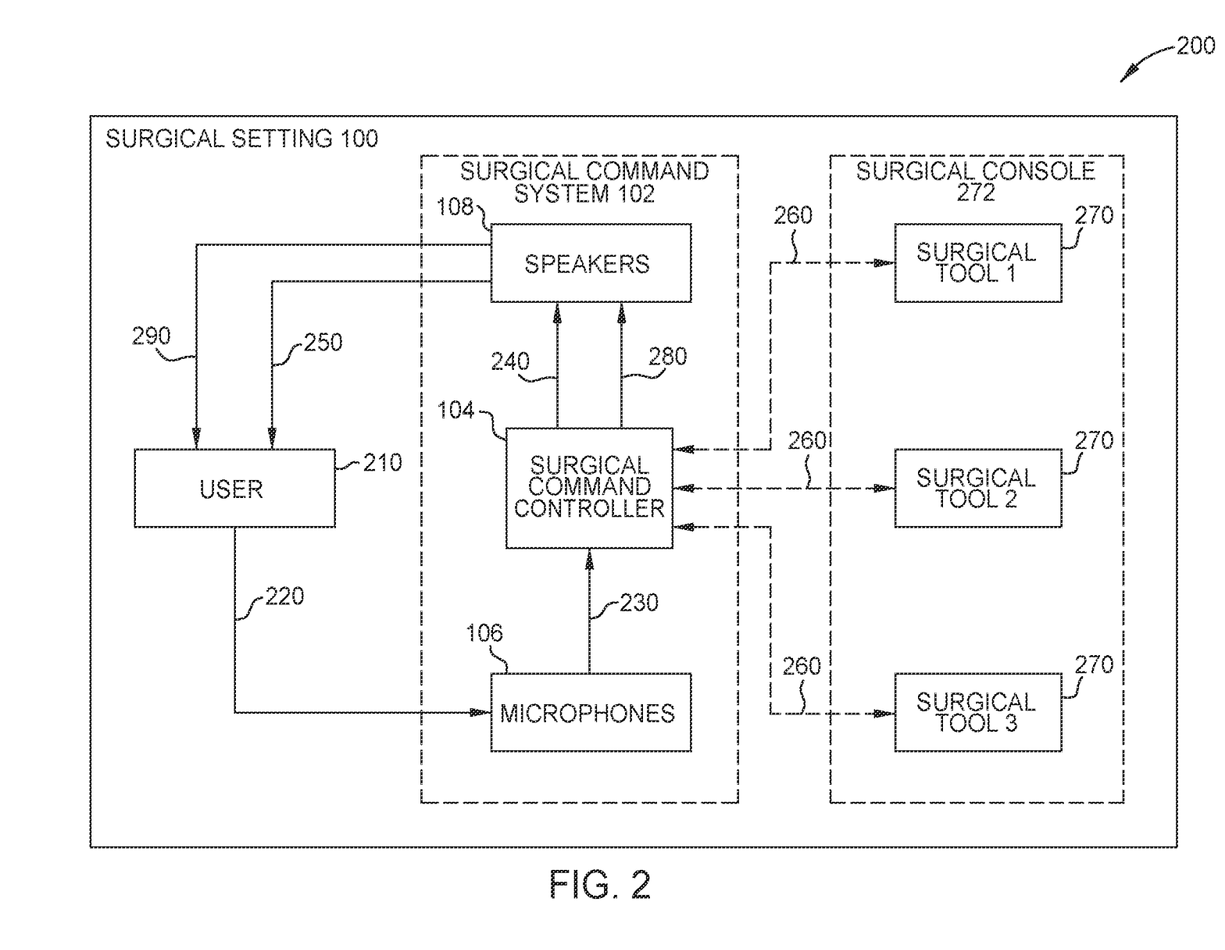
FIG. 2 illustrates a schematic diagram of a voice-controlled surgical command system, in accordance with certain embodiments of the present disclosure.

FIG. 2 illustrates a schematic operational diagram 200 of the voice-controlled surgical command system 102, according to certain embodiments of the present disclosure. As previously described, the surgical command system 102 may be disposed within a surgical setting 100, such as an operating room in which one or more users 210 (e.g., surgeons 150 and/or operating staff) are present. During a surgical procedure, the user 210 generates a voice command 220 which, along with other sounds within the surgical setting 100 (e.g., ambient noise, speech from other users), is captured (e.g., picked up) by the phased microphone arrays 136 of the surgical command system 102. The voice command 220 can be a simple phrase such as, but not limited to, "activate," "deactivate," "increase," and "decrease," or it can be a complex phrase or sentence such as, but not limited to "increase 10%," "decrease 10%," "left 1 millimeter," and "right 1 millimeter," or even more complex phrases and/or sentences. In certain embodiments, the voice command 220 has a layered command architecture, wherein the user 210 selects a desired system, a desired tool (e.g., device), a desired tool mode, and/or a desired task to be performed by the tool, for example, while in the tool mode. Each layer of the layered command architecture (e.g., system, tool, tool mode, and task) may correspond to a set of instructions (e.g., software instructions) that can cause the corresponding surgical system to carry out one or more actions during operation. In still further embodiments, the voice command 220 is a natural language-type voice command 220, which is deciphered via a natural language processing (NLP) module of the surgical command controller 104 with or without pre-programming, described in greater detail below.

Note that although the exemplary voice commands 220 described above are in the English language, the surgical command controller 104 may be configured to support any number of suitable languages, including but not limited to English, Mandarin Chinese, Hindi, Spanish, French, Arabic, Portuguese, Russian, and the like.

As described above, the phased microphone arrays 136 receive the sound waves of the voice command 220, as well as other sounds within the surgical setting 100, and convert the sound waves into one or more audio input signals 230 that are then directly or indirectly relayed to the surgical command controller 104 of the surgical command system 102. Upon receipt of the audio input signals 230, the surgical command controller 104 identifies the voice command 220 in the audio input signals 230 via a speech recognition module, identifies the source of the voice command 220 via positional detection of the user 210 and/or a user identification module, analyzes the voice command 220 via, for example, the NLP module, and maps the voice command 220 to the user 210 (e.g., a user profile) and a defined (e.g., user-defined) set of rules for the user 210. The defined set of rules determine what instructions are to be sent to a corresponding surgical system to carry out a desired action indicated by the voice command 220. In certain embodiments, the defined set of rules may include user-defined actions to be executed upon certain voice commands, as well as user-preferred system settings, tool modes, tool sub-modes, task parameters, and the like. Since multiple users may be present in the surgical setting 100 and use the surgical command system 102 simultaneously, the surgical command controller 104 is configured to identify (e.g., recognize) and distinguish voice commands from each user within the surgical setting 100.

Voice identification is enabled in part due to directional listening by the one or more beamforming, phased microphone arrays 136 distributed within the surgical setting 100, which facilitate sound source localization (i.e., positional detection) and suppression of unwanted operating room noise, such as the speech of operating staff other than the surgeon 150 in certain instances. Additionally, the surgical command controller 104 further includes a user identification module, described in greater detail below with reference to FIG. 3, which works in tandem with the NLP module and may be pre-programmed prior to a surgical procedure for voice recognition. The pre-programming of the user identification module may include a brief, natural language conversational sequence initiated between the surgical command system 102 and one or more users within the surgical setting 100, wherein the surgical command controller 104 learns speech patterns for each of the one or more users. During the surgical procedure thereafter, the user identification module may perform a speech recognition algorithm on voice commands 210 picked up by the phased microphone arrays 136 to identify the source (e.g., user) of the voice commands 210 based on the learned speech patterns.

The ability to identify the source of each voice command enables the surgical command controller 104 to store and associate each user with a predetermined set of commands and/or rules, wherein each set of commands and/or rules may correspond to a different set of instructions to be carried out by a corresponding apparatus. For example, after the surgical command controller 104 analyzes and identifies the voice command 220 as being generated by a particular user 210, the surgical command system controller 104 can map the voice command 220 to a predetermined set of rules for the user 210, which can include preset system settings, tool modes, tool sub-modes, task parameters, and the like for each system and/or device within the surgical setting 100. In certain embodiments, the predetermined set of rules for the user 210 includes associations between simple phrases generated by the user 210 and complex sets of predetermined instructions. For example, a simple phrase such as "display invert" may induce an inversion of heads-up display images with certain color presets preferred by the user 210. The predetermined set of rules for each user may be pre-programmed and stored into the surgical command controller 104 in tandem with the voice recognition pre-programming sequence described above, wherein the surgical command controller 104 learns speech patterns for each user. For example, during a tandem voice recognition and user preset programming sequence, the surgical command system 102 may first request each user to state their name and a device they want to address, followed by requests for desired system and/or device modes and numerical parameters to be associated with corresponding voice commands from the user.

The identification of the source of each voice command further enables the surgical command controller 104 to rank and prioritize voice commands from certain users over others, which may be particularly beneficial when multiple users generate voice commands simultaneously or within a short timeframe. Thus, the surgical command controller 104 may store a predetermined hierarchy of users (e.g., user profiles) from which voice commands may be received, and the predetermined hierarchy is utilized to prioritize voice commands from certain users over others. Alternatively, the surgical command controller 104 may suppress certain voice commands from users determined to be a non-priority.

In tandem with performance of voice recognition, the surgical command controller 104 analyzes the voice command 220 to determine the content thereof and the intent of the user 210. In certain embodiments, analysis includes matching of the voice command 220 to one or more commands previously pre-programmed by the user 210. However, because the surgical command system 102 also supports natural language-type interactions with the user 210, a more complex analysis may also be performed by the NLP module of the surgical command controller 104 to process and decipher (i.e., understand) complex natural language generated by the user 210. Thus, the surgical command system 102 facilitates use thereof without the need for pre-programming or extensive syntax training by the user 210.

After analyzing and mapping the voice command 220 to the user 210, the surgical command controller 104 identifies one or more instructions associated with the voice command 220 and the user 210 that are based on the predetermined set of rules for the user 210. The instructions generally cause one or more actions to be taken or initiated by one or more surgical systems within the surgical setting 100, such as the operating table 120, surgical console 122, heads-up display 124, and microscope 126 depicted in FIG. 1. For example, in certain embodiments, the actions include system and/or device mode selection, system and/or device parameter selection or modification, system and/or device activation and deactivation, actions for controlling operations of surgical tools, data transfer initiation, data recall, data entry, patient profile selection, surgical procedure parameter selection or modification, video and photo control functions (e.g., record, pause, stop, snapshot), display control functions (e.g., image inversion, color preset selection), operative note dictation control functions (e.g., record, stop, save, delete), phone control functions (e.g., answer or place phone calls), and other procedural functions. For ophthalmic surgical procedures, the actions may also include intraocular pressure control via infusion system control, laser (e.g., retinal laser) parameter selection or modification, and the like.

As shown in FIG. 2, the surgical command controller 104 may optionally produce one or more audio output signals 240 based on the identification or non-identification of actions associated with the voice command 220 that are directly or indirectly relayed to the phased loudspeaker array 138. The audio output signals 240 are converted by the plurality of loudspeakers 108 into soundwaves forming an audible response 250 that confirms whether actions have or have not been identified by the surgical command controller 104. For example, in certain embodiments, the loudspeakers 108 may generate a response 250 that includes a summary of the identified actions (e.g., in simple or complex phrases), includes a simple recitation of the voice command 220, or includes a request for further information, clarification, or verification from the user 210, to which the user 210 may respond with another voice command. In certain embodiments, the response 250 may also include a request to the user 210 to confirm or verify that the identified actions are correct. In still further embodiments, the response 250 may indicate to the user 210 that the voice command 220 was not clearly received, and/or that an action has not been identified by the surgical command controller 104. As previously described, the loudspeakers 108 include any suitable beamforming loudspeakers that are arranged and configured to direct the response 250 to desired users within the surgical setting 100. Thus, the soundwaves (i.e., sound wavefront) of the response 250 may be guided directly toward the user 210, thereby improving the ability for the user 210, who generated the voice command, to hear the response 250 and confirm, correct, clarify, or further supplement the voice command 250. In certain embodiments, the response 250 may also be directed by beamforming so as to seem as if it is originating from the surgical system to which the preceding voice command 220 was addressed.

In certain aspects, subsequent to providing the optional response 250, the surgical command controller 104 generates instructions 260 that correspond to the identified tasks and are based on the predetermined set of commands and/or rules for the user 210. The instructions 260 are directly or indirectly provided to one or more desired surgical systems 270 associated with the identified tasks for execution thereof. Accordingly, the instructions 260 indicate to the appropriate surgical systems 270 the tasks identified by the surgical command controller 104 and cause the surgical systems 270 to perform the identified actions, thereby fulfilling the objective of the voice command 220. The instructions 270 may be provided to separate surgical systems 270, or to surgical systems 270 integrated into a single console 272, as shown in FIG. 2. In certain embodiments, a single set of instructions 270 may cause a plurality of surgical systems 270 to execute one or more actions simultaneously or sequentially.

In certain embodiments, the surgical command system 102 further comprises a feedback mechanism that facilitates communication between one or more surgical systems within the surgical setting 100 and the user 210 during or after performance of identified actions. For example, in certain embodiments, the surgical command controller 104 may produce an audio output signal 280 that is converted by the plurality of loudspeakers 108 into an audible response 290 that may convey to the user 210 a warning alert, alarm, progress or status indicator, and any other information relating to the performance of actions by the surgical systems within the surgical setting 100.

Through the inclusion of the components and systems disclosed herein, a surgical setting may be at least partially controlled by voice-activated applications with high confidence, thus providing hands-free operation of surgical systems during the performance of a surgical procedure. The disclosed embodiments allow a surgeon to control various functions of surgical systems without having to stop the surgical procedure to do so. Furthermore, by reducing the amount of physical interaction required to operate surgical devices, the amount of personnel required for the surgical procedure may be reduced, while also reducing the potential risk of bacterial and viral transmission (e.g., contamination) caused by personnel touching the surgical systems.

Figure 3:
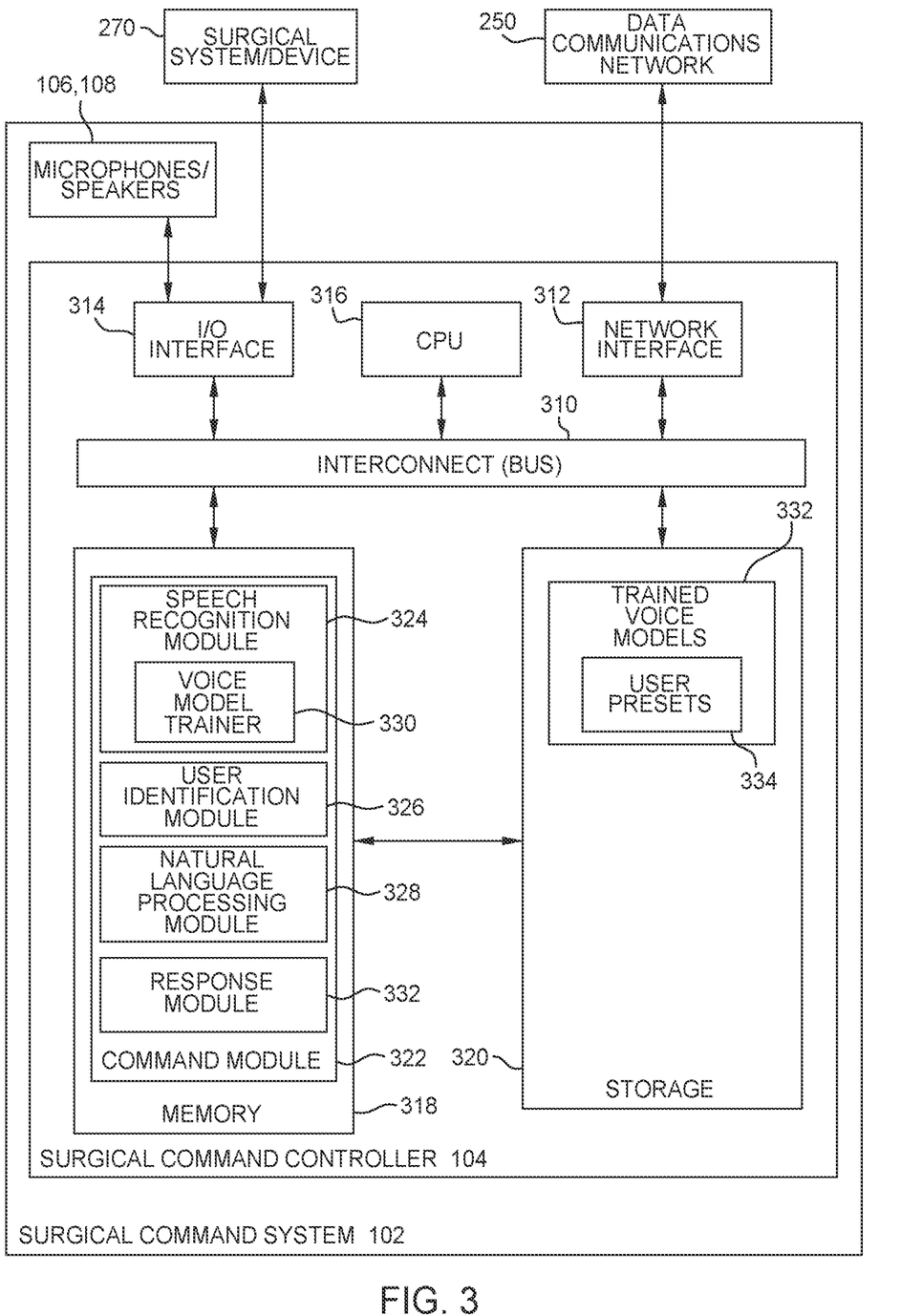
FIG. 3 illustrates exemplary components of the surgical command system of FIG. 2, in accordance with certain embodiments of the present disclosure.

Embodiments of the present disclosure beneficially provide voice-control of a surgical setting with the overall use of the system of which it is a part using a processor and memory within a controller of the surgical system, as shown in FIG. 3, which illustrates exemplary components of the surgical command system of FIGS. 1-2, in accordance with certain embodiments FIG. 3 illustrates an exemplary diagram showing how various components of the surgical command system 102 of FIGS. 1-2 communicate and operate together. As shown, the surgical command system 102 includes, without limitation, the surgical command controller 104, microphones 106, and loudspeakers 108. The surgical command controller 104 includes an interconnect 310, a network interface 312 for connection with a data communications network 350, and at least one I/O device interface 314, which allows for the connection of various I/O devices (e.g., the microphones 106, loudspeakers 108, and surgical systems 270) to the surgical command controller 104. The surgical command controller 104 further includes a central processing unit (CPU) 316, a memory 318, and storage 320. The CPU 316 may retrieve and store application data residing in the memory 318. The interconnect 310 transmits programming instructions and application data, among the CPU 316, the network interface 312, the I/O device interface 314, the memory 318, and the storage 320, etc. The CPU 316 can represent a single CPU, multiple CPUs, a single CPU having multiple processing cores, and the like. Additionally, the memory 318 represents random access memory.

The storage 320 may be a disk drive. Although shown as a single unit, the storage 320 may be a combination of fixed or removable storage devices, such as fixed disc drives, removable memory cards or optical storage, network attached storage (NAS), or a storage area-network (SAN). Further, the storage 320 may comprise trained voice models 332 of users within a surgical setting, which includes user presets 334. User presets 334 comprise discrete sets of rules associated with each user in a surgical setting that are applied by the surgical command system 102 to generate instructions to be carried out by a corresponding system and/or device in response to a voice command by a user.

The memory 318 comprises a command module 322 that includes instructions, which when executed by the processor, performs an operation for controlling the surgical command system 102, as described in the embodiments herein. For example, according to embodiments described herein, the memory 318 includes a speech recognition module 324 which comprises executable instructions for recognizing (i.e., identifying) speech, such as a voice command, in an audio input signal received from the microphones 106. In addition, the memory 318 includes a user identification module 326 having a voice model trainer 330, which comprises executable instructions for pre-programming of voice commands, learning speech patterns of users, and mapping the speech identified by the speech recognition module 324 to a corresponding user. The memory 318 further includes a natural language processing (NLP) module 328 which comprises executable instructions for analyzing and deciphering natural language voice commands (e.g., matching natural language to tasks). Furthermore, the memory 318 includes a response module 332 comprising executable instructions for generating audio output signals based on information received from the speech recognition module 324 to enable bi-direction communication between the surgical command system 102 and a user.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. A surgical command system, comprising:
one or more microphones coupled to a processor and configured to convert sound waves within a surgical operating environment to one or more audio input signals;
one or more loudspeakers coupled to the processor and configured to generate sound waves within the surgical operating environment based on one or more audio output signals received directly or indirectly from the processor;
a memory comprising executable instructions; and
the processor in data communication with the memory and configured to execute the instructions to cause the surgical command system to:
receive directly or indirectly the one or more audio input signals from the one or more microphones;
identify one or more speech commands in the one or more audio input signals;
map at least one of the one or more speech commands to a user in the surgical operating environment;
identify one or more actions associated with the at least one of the one or more speech commands;
indicate the one or more actions to a surgical device to cause the surgical device to perform the one or more actions;
cause the one or more audio output signals to be produced based on the one or more actions; and
cause the one or more loudspeakers to generate outgoing speech responses based on the one or more audio output signals.

2. The surgical command system of claim 1, wherein the surgical command system is further configured to determine a location of a source of the one or more speech commands in the one or more audio input signal.

3. The surgical command system of claim 2, wherein the location of the source is utilized to map the one or more speech commands to the user.

4. The surgical command system of claim 1, wherein the surgical command system is further caused by the processor to actively reduce continuous ambient noise in the one or more audio input signals from the one or more microphones.

5. The surgical command system of claim 1, wherein the surgical command system is further caused by the processor to perform echo cancellation on the one or more audio input signals from the one or more microphones.

6. The surgical command system of claim 1, wherein the one or more actions comprise one or more of a surgical device selection, mode selection, and task selection.

7. The surgical command system of claim 1, wherein the one or more actions are identified at least partially based on a user profile associated with the user and accessible to the processor.

8. The surgical command system of claim 7, wherein the user profile comprises mappings of different actions to different speech commands, and wherein the mappings include a mapping between one or more of the different actions and one or more of the different speech commands.

9. The surgical command system of claim 1, wherein:
the processor being configured to map the at least one of the one or more speech commands to the user further comprises the processor being configured to map each of the one or more speech commands to a corresponding user in a group of users including the user,
the processor further configured to prioritize the at least one of the one or more speech commands and/or the one or more actions based on a predetermined hierarchy of the group of users, wherein the predetermined hierarchy indicates a higher rank for the user compared to other users associated with the one or more speech commands.

10. The surgical command system of claim 1, wherein the outgoing speech response comprises an announcement of the one or more actions indicated to the surgical device.

11. The surgical command system of claim 10, wherein the outgoing speech response is relayed from the one or more loudspeakers in a direction of the user mapped to the identified one or more speech commands.

12. The surgical command system of claim 1, wherein the one or more loudspeakers include a plurality of loudspeakers arranged in a phased loudspeaker array.

13. The surgical command system of claim 12, wherein the phased loudspeaker array is arranged to perform transmit beamforming for transmitting soundwaves within the surgical operating environment.

14. The surgical command system of claim 1, the one or more microphones include a plurality of microphones arranged in a phased array microphone array.

15. The surgical command system of claim 14, wherein the phased microphone array is arranged to perform receive beamforming for receiving soundwaves within the surgical operating environment.

16. The surgical command system of claim 1, wherein the one or more microphones are located in a surgical mask worn by the user in the surgical operating environment.

* * * * *